United States Patent [19]
Pering et al.

[11] Patent Number: 5,503,160
[45] Date of Patent: Apr. 2, 1996

[54] DYNAMIC FILTER FOR REAL-TIME ARTIFACT REMOVAL FROM WAVEFORMS

[75] Inventors: Richard D. Pering, Palo Alto; Don Goodnature, Santa Clara; James M. Lindauer, San Francisco, all of Calif.

[73] Assignee: Hewlett-Packard Company, Palo Alto, Calif.

[21] Appl. No.: 134,780

[22] Filed: Oct. 12, 1993

[51] Int. Cl.⁶ ........................................................ A61B 5/08
[52] U.S. Cl. ........................... 128/706; 128/695 R; 607/9
[58] Field of Search ...................................... 128/630, 668, 128/670–672, 680, 687, 688, 693, 695, 696, 700, 706, 708

[56] References Cited

U.S. PATENT DOCUMENTS

| | | | |
|---|---|---|---|
| 4,781,201 | 11/1988 | Wright et al. | 128/706 |
| 5,188,117 | 2/1988 | Steinhaus et al. | 128/708 |

FOREIGN PATENT DOCUMENTS

| | | | |
|---|---|---|---|
| 2589713 | 5/1987 | France | 128/700 |

*Primary Examiner*—William E. Kamm
*Assistant Examiner*—Marianne Parker

[57] ABSTRACT

During sampling, a finite impulse response (FIR) filter separates a composite signal into two components, non-cardiac physiological phenomena and cardiac artifacts. The length of the filter window dynamically varies to produce an output signal in which the cardiac frequency and any associated harmonics are suppressed. The FIR filter is applied to the patient signal and lags the patient signal by at least one interval between triggering events. When the present interval between triggering events passes by the filter window, the window length is gradually adjusted to have the same length as the next period such that the triggering events are synchronized with the endpoints of the filter window at the start of each interval. The difference between the present interval and the next interval is evenly distributed or subtracted across the filter window between synchronizations.

12 Claims, 8 Drawing Sheets

DYNAMIC FILTER FOR REAL-TIME ARTIFACT REMOVAL FROM WAVEFORMS

FIELD OF THE INVENTION

The invention pertains generally to patient monitors and more particularly to an apparatus and method for isolating physiological phenomena in real-time by removing cardiac artifacts that occur at a varying cardiac frequency and harmonics of that frequency.

BACKGROUND OF THE INVENTION

Transducers are commonly used in patient monitoring to gather information about a patient's condition. The resulting signals are often a mixture of physiological phenomena. In general, this is an inherent property in all electrical and pressure signals derived from mechanical movement in the body, in particular, organ movement such as that by the diaphragm and the heart. Unfortunately, the intrinsic characteristics of these measured signals are often overwhelmed by the strength of the artifacts introduced by the heart. Of the organs, the heart usually has the most pronounced and most rapid motion, which can be picked up very easily by the transducers when measuring another phenomenon. In other words, the electrical signals from the heart often "drown out" the signals of interest. For example, respiratory impedance is a mixture of electrical changes due to respiration and electrical changes due to mechanical cardiac events. Observing each phenomena in isolation is desirable for medical analysis and patient monitoring.

One technique to isolate the phenomena is fixed-frequency filtering. This method has limited success since the frequency ranges overlap for heart and respiration rates. As a result, removing the cardiac artifacts at fixed frequencies often fails altogether or significantly distorts the filtered respiration signal. Since the physiological artifacts, such as those due to cardiac or other muscle activity, vary in time with response to stress and illness, fixed-frequency filtering is ineffective at artifact removal.

In "Canceling the Cardiogenic Artifact in Impedance Pneumography", IEEE/Seventh Annual Conference of the Engineering in Medicine and Biology Society, pp 855–859, Sahakian et al attempted adaptive filtering by applying a cardiac artifact template which was then subtracted from the respiratory impedance (RI) waveform. The timing signal for adapting the signal averaged cardiac artifact template was the output of a conventional QRS detector. The QRS detections further provided the pacing for subtracting the cardiac artifact template from the RI waveform. This technique failed to take into account the beat-to-beat variations in the amplitude and shape of the cardiac artifact: the shape of the current cardiac artifact is often significantly different from that of the signal-averaged cardiac artifact, so that simply subtracting the averaged cardiac artifact is often ineffective and may even introduce new artifacts. Furthermore, template-adaptive filtering is not responsive enough to remove beat-to-beat variations.

In the "Elimination of Breathing Artifacts from Impedance Cardiograms at Rest and During Exercise", Medical and Biological Engineering & Computing, January 1988, pp 13–16, Eiken and Segerhammer experimentally reduced breathing artifacts contained in an impedance cardiogram by using a moving-window technique in conjunction with linear regression analysis. The window length had a width that was jump adapted at the start of each new cardiac cycle to be equal to the length of the previous cardiac cycle. Using the sample points within this window, they then performed a linear regression to find a straight line segment that was the "best" straight line approximation to the data within the window. Finally, the center point of the regression line was used to estimate the value of the respiration signal with the cardiac artifact removed. The window length was updated and a linear regression analysis was performed when the center sample passed the R-beat. This technique was inadequate for two reasons: linear regression is computationally expensive and jump adaptation introduces artifacts into the resulting filter output.

SUMMARY OF THE INVENTION

In real time, a finite impulse response (FIR) rectangular filter separates a composite patient signal into two components: non-cardiac physiological phenomena and cardiac artifacts as the signal is being sampled. The length of the filter window is dynamically varied to produce a smooth output signal in which effects of a varying cardiac frequency and any associated harmonics are suppressed. The varying cardiac frequency is determined by marking the cardiac events in a reference cardiac signal. When the present interval between triggering events passes by the filter window, the window length is gradually adjusted to have the same length as the next period when the leading edge of the window is synchronized with one of the cardiac events. Thus, there is a time-average analysis for each time the filter window is advanced by a sample. The difference between the present interval and the next interval is evenly distributed across the filter window between synchronizations.

DETAILED DESCRIPTION OF THE PREFERRED EMBODIMENTS

Figure 1:
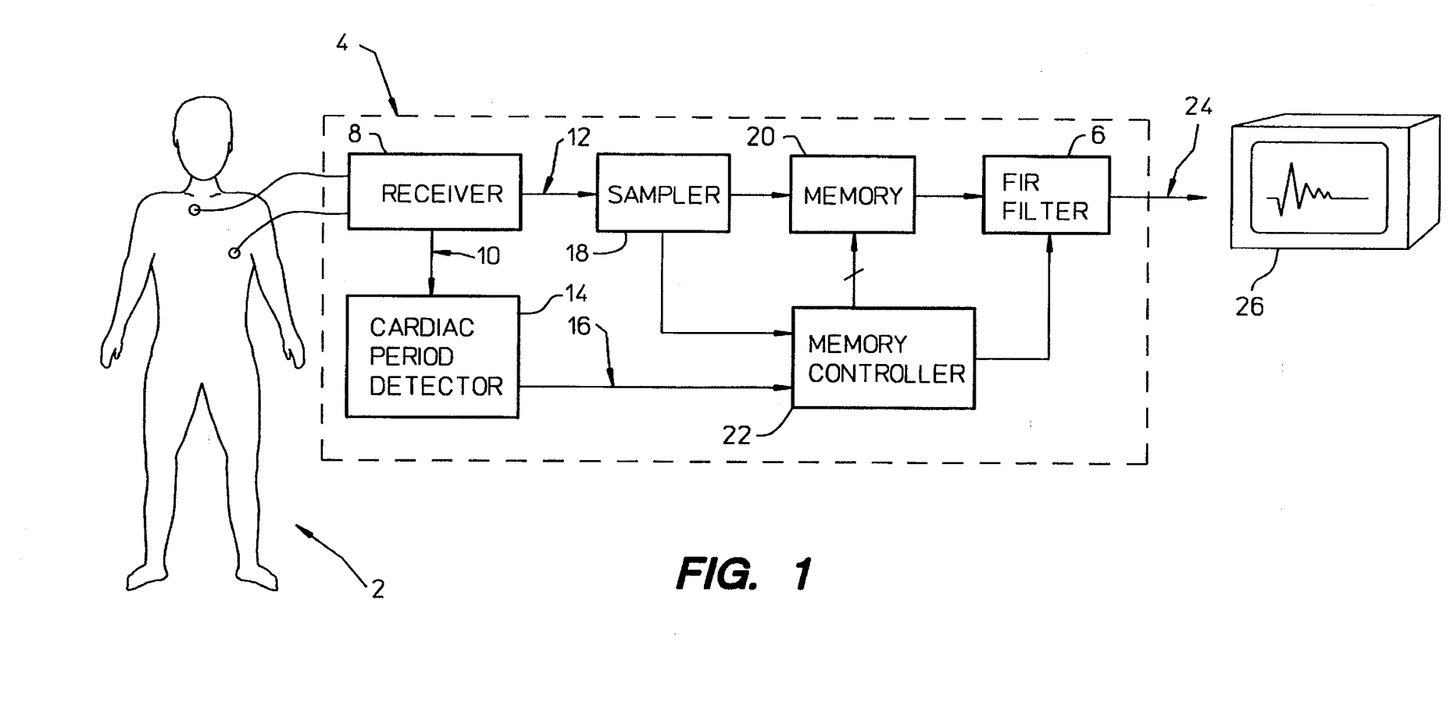
FIG. 1 is a block diagram that shows the main electrical components of the invention, which is shown attached to a patient.

FIG. 1 shows a patient 2 attached to a patient monitor 4 that has a dynamically varying filter 6, preferably one that has a finite impulse response (FIR). At least two physiological signals from the patient 2 are measured, for example, as voltages by a receiver 8: a cardiac signal 10 and a composite signal 12 that contains physiological phenomena such as respiratory impedance or central venous pressure. Signals from all of the patient's physiological phenomena are assumed to be contaminated by the cardiac signal 10.

Initially, a cardiac period detector 14 detects cardiac events contained within the cardiac signal 10 and determines a cardiac frequency, which can vary between the cardiac events, and produces a window variable 16. At the same time, the sampler 18 digitally samples the composite signal 12, which is then stored in memory 20. A memory controller 22 uses the window variable 16 to adjust the length of the finite impulse response (FIR) filter 6, which may be a rectangular filter, and applies the FIR filter to the sampled data stored in memory. The FIR filter 6 produces a filtered composite signal 24 in which the non-cardiac phenomenon corresponds to the dominant component.

The filtered composite signal 24 that represents the non-cardiac phenomena can be displayed on a conventional monitor 26 or further analyzed by a computer (not shown) to detect periodic events in the non-cardiac signal; this is explained in greater detail below. If the non-cardiac events are not within a predetermined tolerance region, an indicator of an abnormal patient condition is activated. Furthermore, the out-of-tolerance non-cardiac signal may be displayed on the monitor 26.

Figure 2:
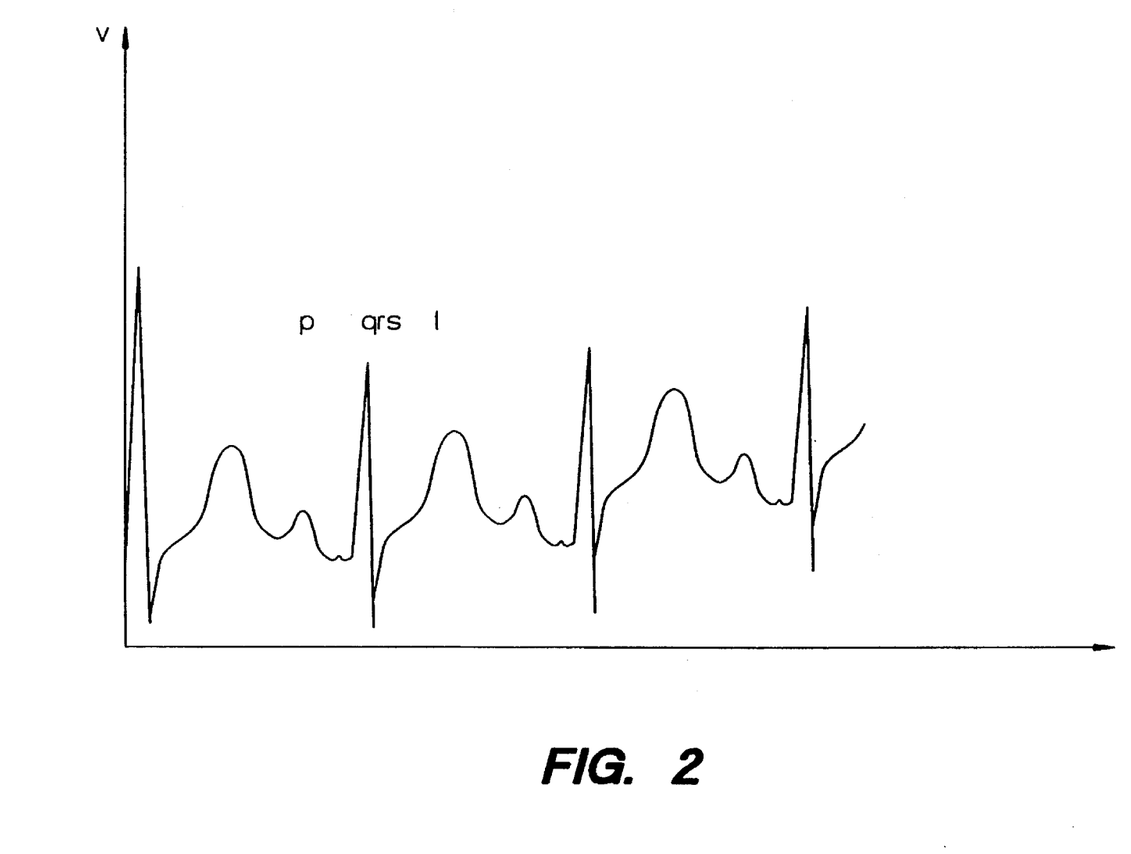
FIG. 2 illustrates an electrical representation of a cardiac event.

FIG. 2 is an electrical representation of a series of cardiac events. Since the cardiac frequency varies with physical activity, stress, and condition of the patient, the events are preferably detected from some relatively constant feature of the cardiac signal 10, such as peak voltage. The cardiac event is a composite of well-known "PQRST" waves. The P wave corresponds to the depolarization of the atria; the length of the P wave indicates the time necessary to depolarize the atria. The QRS wave reflects the spread of depolarization through the ventricles. The amplitude of the QRS wave is much greater than that of the P wave because the ventricles have more tissue mass than the atria. During the QRS wave, the atria repolarize. The ventricles remain depolarized during the ST wave. The T wave is generated as the ventricles repolarize.

Figure 3:
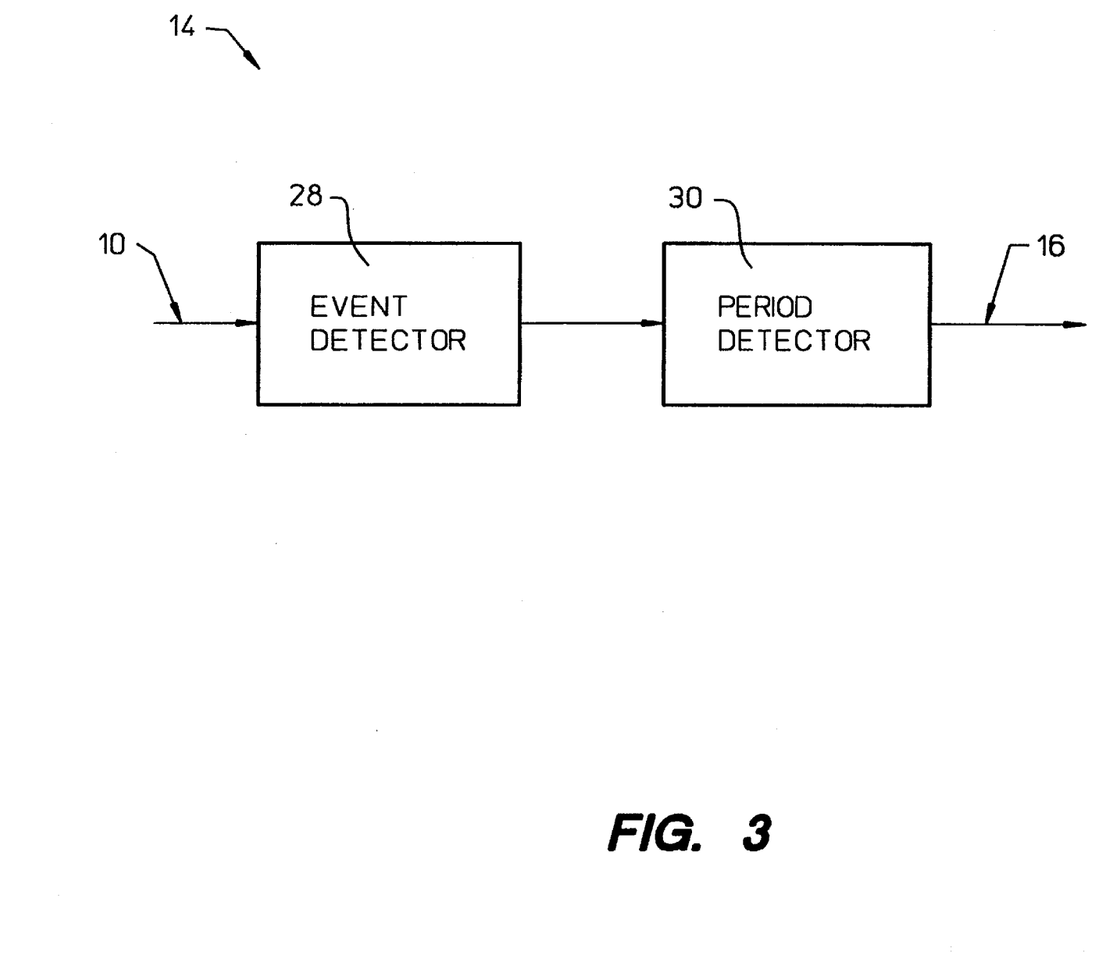
FIG. 3 is a functional block diagram of a cardiac period detector in FIG. 1.

FIG. 3 is a functional block diagram of the cardiac period detector 14 shown in FIG. 1. The cardiac period detector 14 is composed of a cardiac event detector 28 and a cardiac interval detector 30. The event detector 28 receives the cardiac signal 10 and searches for the reference points in the cardiac signal 10. The cardiac interval detector 30 is connected to the cardiac event detector 28. The interval detector 30 counts the number of samples between adjacent cardiac events and produces the cardiac interval 16. The cardiac interval 16 is defined as the number of samples that are taken between adjacent cardiac events, preferably at a constant sampling rate. The cardiac interval 16 is updated at each event detection to indicate the variable cardiac period. Any portion of the QRST wave can be used as reference point and thus defines a cardiac event.

The cardiac period detector 14 can be constructed by any technique known to those in the art, such as those suggested by Freisen et al. in "A Comparison of the Noise Sensitivity of Nine QRS Detection Algorithms", IEEE Transactions Biomedical Engineering, p. 85–98 (1990).

Figure 4:
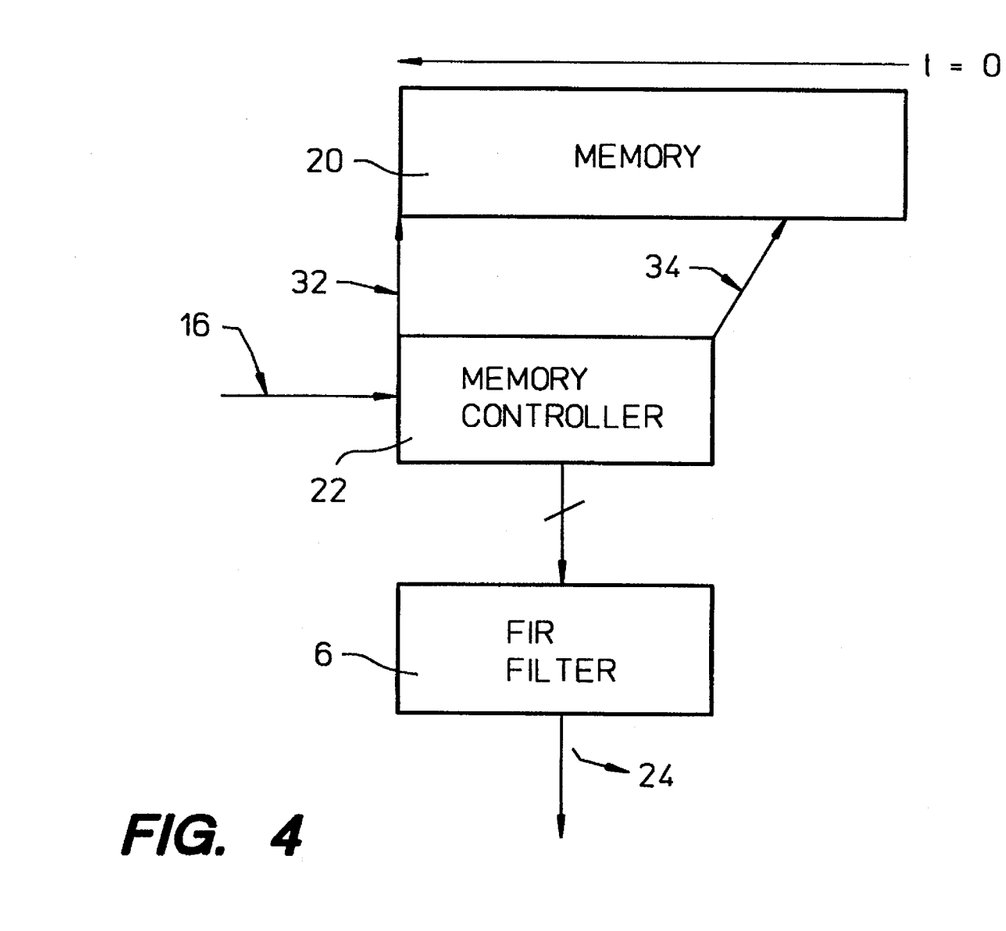
FIG. 4 is a functional block diagram of an arrangement for controlling the window length of the FIR filter shown in FIG. 1.

FIG. 4 is a functional block diagram of an arrangement for controlling the window length of the FIR filter shown in FIG. 1. The filter has a window length that is dynamically adjusted to match the window variable such that the window length (in time) coincides with the period of cardiac events when one of the window edges is at a cardiac event. A rectangular filter provides the optimal reduction of the cardiac frequency and its harmonics. The rectangular filter, as is well-known, is a type of symmetrical moving-average filter with equal weights.

The window length is gradually adjusted to correspond to a complete cardiac cycle. As the start edge of the window advances sample by sample, the window length is smoothly adapted toward the next cardiac cycle so as to avoid sudden jumps in the filter output. Without the gradual adjustment of the window length, the resulting time-averaged signal would introduce distortion.

According to the invention, the window length is set equal to the interval between two adjacent cardiac events. The cardiac interval is chosen as the window length because the cardiac frequency and any associated harmonics will then be cancelled or "notched out" of the non-cardiac signal during averaging using any symmetric filter. Thus, the FIR filter is designed to have the "zeros" of the transfer function at the harmonics of the cardiac frequency. The zeros appear as periodic "holes" in the impulse response when viewed in the frequency domain. An additional constraint (the well-known Nyquist criterion) is that the sampling rate must be selected to be at least twice the highest frequency of the phenomena of interest in the composite signal to avoid aliasing.

The properties of a finite impulse response (FIR) filter are well known in the art and are described in many standard texts on digital signal processing or time series analysis. An FIR filter can be described roughly as a type of signal averaging and weighting device that moves or "sweeps" over a series of values. The general structure of an FIR filter can be represented as follows:

$$y(t) = \sum_{m=0}^{n-1} w(m) \cdot x(t-m) \qquad \text{Eqn. 1}$$

where y(t) is the output value of the filter at time t;

x(t-m) is the input value to the filter m time units before time t; and w(m) is the m'th of a set of n weighting factors.

In other words, the output y(t) from the FIR filter at any given time t is formed as a weighted sum of the most recent input value x(t) and the n-1 previous input values x(t-1), x(t-2), . . . , x[t-(n-1)]. Weighting is done by multiplying each input value x(t-m) m time units ago by the corresponding m'th weight value w(m). If the weights w(m) are different, then some of the input values are allowed to contribute more to the output value than others. If all the weights are the same, in particular, if they are all set equal to one, then the FIR filter is said to be rectangular.

Note that at the next time period (t increases by one), the previous "oldest" input value x[t-(n-1)] will be more than n time units old and will not contribute to the sum that forms the output value. No matter what the input value is, its "influence" on the output will be finite: it will not last more than n time units. In other words, the response of the filter even to impulse-like input signals is finite.

Alternatively, other known symmetric FIR filters, such as the Hamming, Hanning, and Blackman, may be used, but at the cost of efficiency. Asymmetric filters, in combination with symmetric or asymmetric filters may also be used, as long as the overall filter response has zeros at the cardiac frequency and its harmonics and thus notches out events occurring at these frequencies. Modulating the window size controls which frequencies the filter will notch out. The preferred rectangular filter may be constructed by methods known to those versed in the art.

Figure 5:
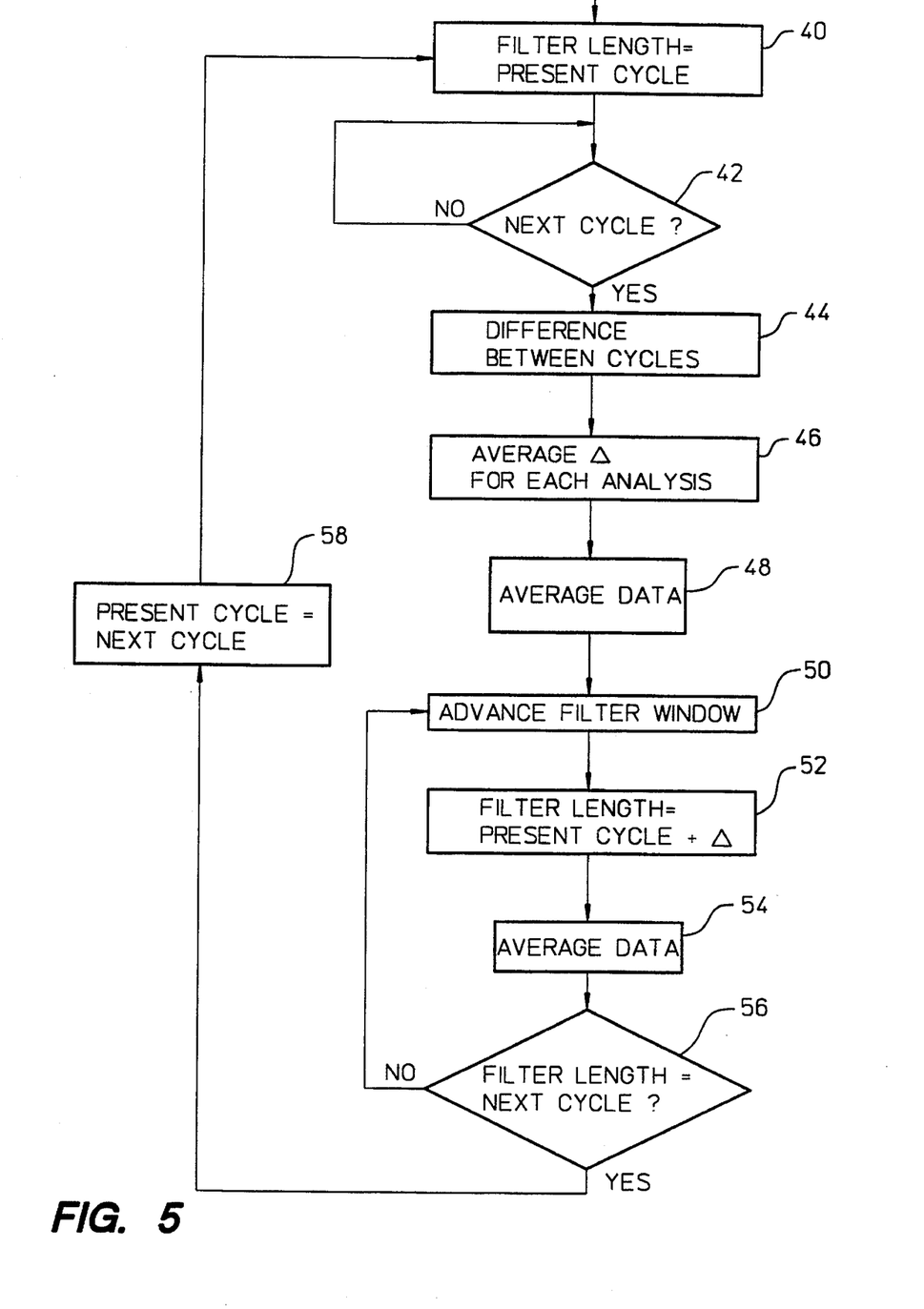
FIG. 5 shows the process diagram for distributing a next cardiac interval as a filter window moves across a series of cardiac data values.

FIG. 5 shows a flowchart of the process for distributing the next cardiac interval as the filter window traverses from the present cardiac interval to the next cardiac interval. The present cardiac interval is chosen to be the FIR filter length. The next cardiac interval is determined from the series of cardiac events. The difference between the present cardiac interval and the next cardiac interval is determined. This difference is then distributed over the number of samples in the present cardiac interval. The length of the filter determines the number of samples to be averaged. The filter window is advanced by one sample while the filter length is updated by the pro-rated difference. The filter length is updated until the filter length equals the next cardiac interval. At this point, the next cardiac interval becomes the present cardiac interval and the distribution process is repeated.

Figure 6:
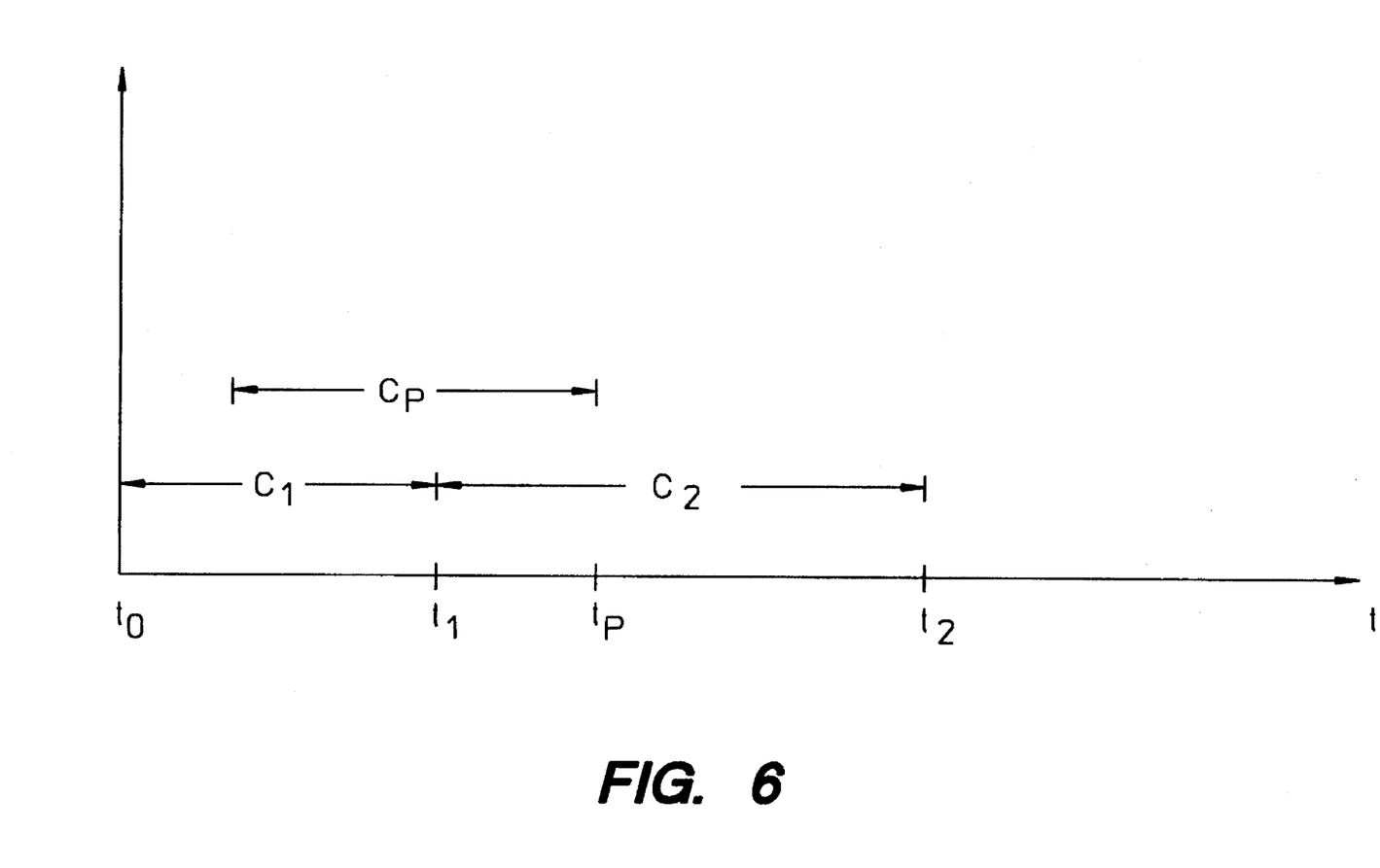
FIG. 6 illustrates a general application of dynamically adapting the window length of the FIR filter.

FIG. 6 illustrates a general application of dynamically adapting the window length of the FIR filter. $C_1$ and $C_2$ are two adjacent cardiac intervals. Although the cardiac intervals were sampled at the same sampling rate, they are of different durations thus, $C_2$ contains more samples than $C_1$. As shown in Equation 2, at time $t_1$, the window length in time, $W_p$, is equal to the first cardiac length, $C_1$.

$$W_p = C_1 + \frac{(C_2 - C_1)}{(t_2 - t_1)} (t_p - t_1) \qquad \text{Eqn. 2}$$

When $t_p > t_1$, $W_p$ is the sum of the first cardiac interval $C_1$ and a fraction of the difference between $C_2$ and $C_1$. Since $C_2$ is equal to $(t_2-t_1)$, Equation 2 may also be expressed as:

$$W_p = C_1 + \frac{(C_2 - C_1)}{C_2} (t_p - t_1) \qquad \text{Eqn. 3}$$

As partial samples cannot be averaged, the window length is updated such that $W_p$ corresponds to an integral number of samples.

$$N_p = W_p \cdot S \qquad 4$$

The number of samples corresponding to a window length, $N_p$, of any FIR filter, is described in Equation 4, in which S is the sampling frequency in hertz. Thus, the length of the filter is the product of the window variable and the sampling rate.

This method dynamically varies the length of the filter window to produce a smooth output signal in which cardiac phenomena are suppressed. After the present interval between cardiac events passes by the filter window, the window length coincides with the cardiac interval when either one of the window edges is at a cardiac event. This adjusts the position of the "zeros" of the filter to be at the cardiac frequency and its harmonics, thus notching out any cardiac artifacts at those frequencies. The difference between the present interval and the next interval is evenly distributed across the filter window between synchronizations. The evenness in distribution is dependent both on the sampling frequency and the difference between the cardiac intervals. Higher sampling frequencies allow smoother adaptation.

The filter length is adjusted by the memory controller 22, which is connected to the memory 20 and the cardiac period detector 14. The controller 22 has two pointers, a newest sample pointer 32 and an oldest sample pointer 34, which define which samples (in particular, how many) in memory 20 are to be averaged. The memory controller 22 advances the newest sample pointer 32 by one composite sample for every sampling period and gradually adjusts the oldest sample pointer 34 such that the length of the adaptive window is the cardiac interval 16 when the newest sample pointer 32 is at one of the reference points. The memory controller 22 takes the difference between the next cardiac period and compares it to the current cardiac period. This difference will be evenly distributed over the filter length by the memory controller 22 in whole samples.

For example, if the number of samples in the current cardiac period is 80 and the number in the next cardiac period is 100, the filter length must be lengthened by 20 samples. One way to evenly distribute the difference is by not advancing the oldest sample pointer every fifth averaging across the data. Thus, the filter length increases every fifth averaging.

Figure 7:
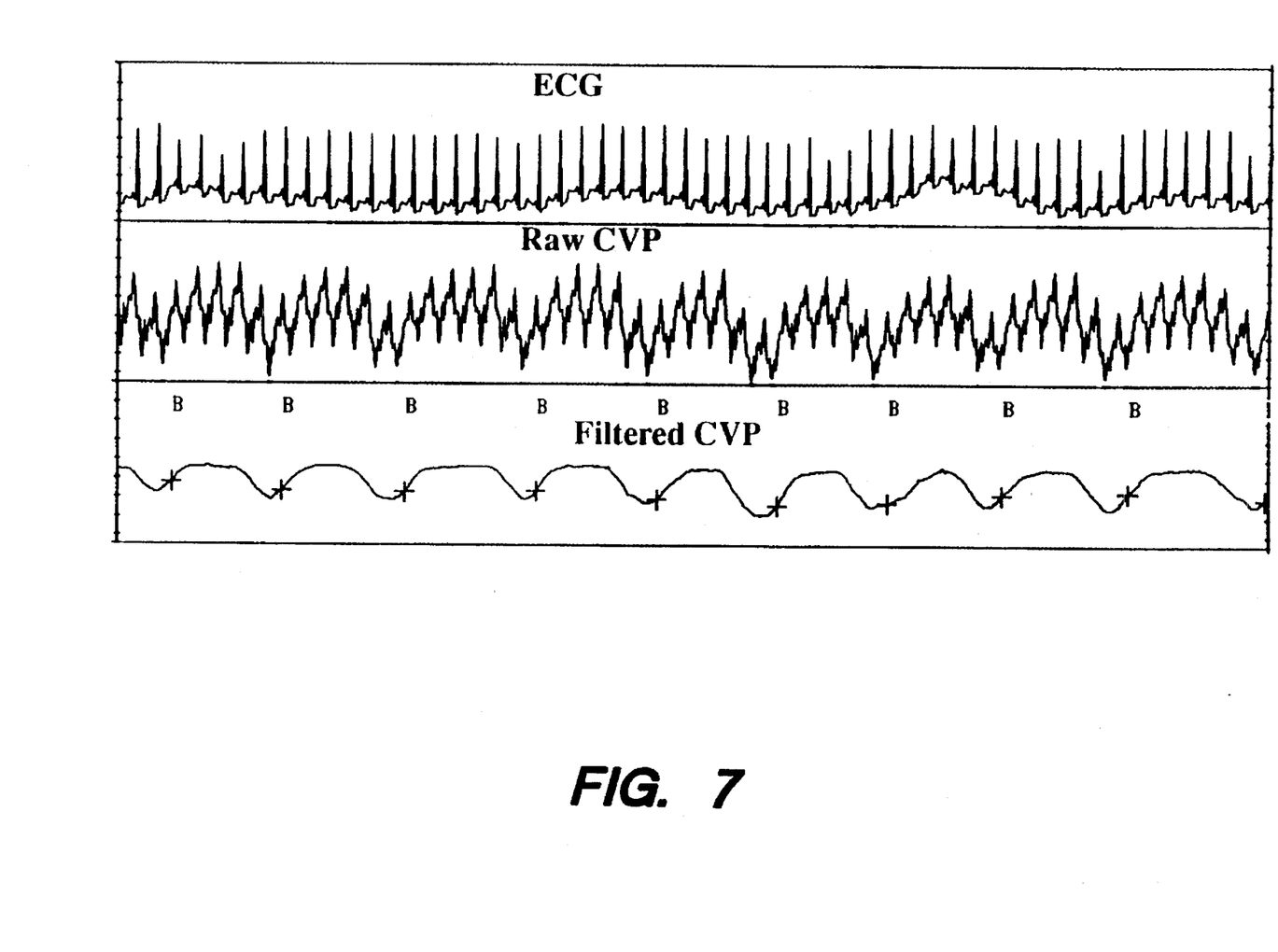
FIG. 7 shows the different stages of filtering the patient signal using the invention.

FIG. 7 shows the different stages of filtering the composite signal. The ECG signal is taken as the cardiac signal 10 and the central venous pressure (CVP) signal is used as the composite signal 12, which contains cardiac artifacts. The filtered CVP signal, a time average of the sampled composite signal minus the cardiac frequency and associated harmonics, can be used for subsequent analysis by a computer or by trained medical personnel: trained medical personnel are :much better at pattern recognition, i.e. visually curve fitting the original signal, while a computer can monitor patients simultaneously without fatigue. Thus, a time-averaging method allows the computer to assist with monitoring the patients. The composite signal is modulated by notching out the cardiac frequency and any associated harmonic frequencies. The filtered composite signal can be further analyzed to show signal features such as peaks and valleys.

Figure 8:
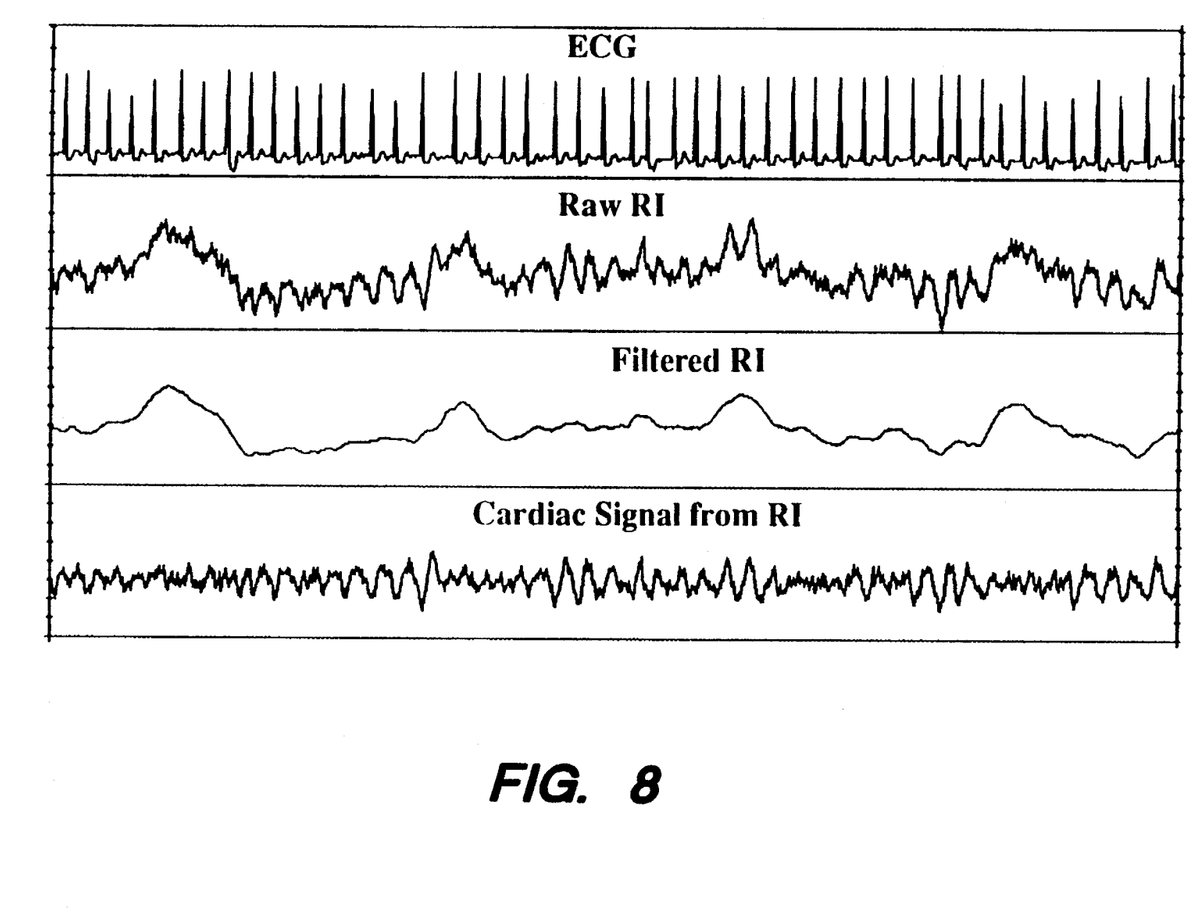
FIG. 8 shows the results of subsequent processing of the composite signal to provide additional cardiac information.

FIG. 8 shows subsequent processing of the non-cardiac signal to provide additional cardiac information. The ECG signal is taken as the cardiac signal 10 and the respiratory signal (RI) is used as the composite signal 12 which contains cardiac artifacts. The filtered respiratory signal is subtracted from the unfiltered respiratory signal. The result is a cardiac signal having reduced non-cardiac effects. Removal of the respiratory artifact provides the pure cardiac impedance signal with minimal respiratory distortion.

We claim:

1. A patient monitor, receiving a cyclical cardiac signal and a composite signal containing cardiac artifacts from a patient, comprising:

a sampler, detecting the composite signal at a fixed rate, generating composite samples from the composite signal;

a cardiac event detector, detecting the cyclical cardiac signal, a marked stable reference point for each cardiac cycle;

a cardiac interval detector detecting the marked stable reference points and generating a cardiac output signal having a variable cardiac frequency and associated harmonics, wherein the variable cardiac frequency corresponds to a cardiac interval between adjacent marked stable reference points;

memory, detecting and storing the composite samples, having a newest and an oldest composite sample pointer;

a first digital filter, connected to the memory, having an adaptive window with two edges defining a length, wherein one edge corresponds to the newest composite sample pointer and the other edge corresponds to the oldest composite sample pointer, for removing events which occur at the variable cardiac frequency and the associated harmonics and producing a filtered composite signal; and memory controlling means connected to the memory and detecting the cardiac output signal, for advancing the newest composite sample pointer by one composite sample and gradually adjusting the oldest composite sample pointer such that the length of the adaptive window is equal to the cardiac interval when the newest composite sample pointer is at one of the marked stable reference points;

wherein the filtered composite signal is produced by removing events which occur at the variable cardiac frequency and the associated harmonics of the cardiac frequency from the composite signal such that the cardiac artifacts are reduced.

2. A patient monitor as defined in claim 1, wherein the first digital filter is a finite impulse response filter.

3. A patient monitor, as defined in claim 2, further comprising:

a feature extractor detecting the filtered composite signal, generating a first output signal having a frequency which corresponds to signal features of the filtered composite signal, and a second output signal which corresponds to durations between the signal features; and a rate detector, detecting the second output signal and generating a rate output signal corresponding to the first output signal.

4. A patient monitor as defined in claim 3, further comprising:

a patient condition indicator;

evaluation means, connected to the patient condition indicator and the rate detector, for evaluating the rate output signal with at least one patient threshold and activating the patient condition indicator.

5. A patient monitor as defined in claim 4, further comprising a second finite impulse response filter detecting the filtered composite signal and the composite signal, generating an output signal by subtracting the filtered composite signal from the composite signal.

6. A patient monitor as defined in claim 2, wherein the first finite impulse response filter has means for adapting zeros which correspond to the varying cardiac frequency and its harmonics.

7. A patient monitor as defined in claim 6, wherein the first finite impulse response filter is a rectangular filter.

8. A patient monitor as defined in claim 1, further comprising a second finite impulse response filter, detecting the filtered composite signal and the composite signal, generating an output signal by subtracting the filtered composite signal from the composite signal.

9. A filtering method for reducing cardiac artifacts in a composite signal by receiving from a patient a first, second, and third cardiac event and a composite signal containing cardiac artifacts, the filtering method comprising the steps of:

measuring a first and a second cardiac period, wherein the first cardiac period is a duration between the first and second cardiac events, wherein the second cardiac period is a duration between the second and third cardiac events;

sampling the composite signal at a sampling rate so as to produce discrete composite values;

storing the discrete composite values in a series of memory addresses;

defining a window correction factor by dividing a difference between the first and second cardiac periods by the sampling rate;

pointing a first pointer to an address in the memory addresses containing the discrete composite value corresponding to the first cardiac event and a second pointer to the address containing the discrete composite value corresponding to the second cardiac event; and producing a filtered composite signal using a finite impulse response filter having a dynamic window length, the step of producing comprising:

averaging the discrete composite values between the first and second pointers, inclusively, updating the first pointer to the next discrete composite value and the second pointer such that the dynamic window length is changed at multiples of the window correction factor when the multiples correspond to an integral number of discrete composite values, and repeating, the steps of averaging, and updating until the first pointer points at the address containing the discrete composite value corresponding to the second cardiac event.

10. A filtering method as defined in claim 9, further comprising the steps of:

detecting signal features of the filtered composite signal; and determining a rate at which the signal features occur.

11. A filtering method as defined in claim 10, further comprising the steps of:

evaluating the rate with a patient threshold; and activating an alarm when the rate is less than the patient threshold.

12. A filtering method as defined in claim 11, further comprising the step of subtracting the filtered composite signal from the composite signal such that the filtered composite signal is substantially removed from the composite signal.

* * * * *